United States Patent
Kulkarni et al.

(10) Patent No.: US 9,835,535 B2
(45) Date of Patent: Dec. 5, 2017

(54) SHEAR THINNING CALIBRATION FLUIDS FOR RHEOMETERS AND RELATED METHODS

(71) Applicant: Halliburton Energy Services, Inc., Houston, TX (US)

(72) Inventors: Sandeep D. Kulkarni, Kingwood, TX (US); Jacob Michael Sieverling, Kingwood, TX (US); Dale E. Jamison, Humble, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 85 days.

(21) Appl. No.: 14/770,501

(22) PCT Filed: Oct. 31, 2014

(86) PCT No.: PCT/US2014/063388
§ 371 (c)(1),
(2) Date: Aug. 26, 2015

(87) PCT Pub. No.: WO2016/068991
PCT Pub. Date: May 6, 2016

(65) Prior Publication Data
US 2016/0363519 A1    Dec. 15, 2016

(51) Int. Cl.
*G01N 11/00* (2006.01)
*G01N 11/14* (2006.01)

(52) U.S. Cl.
CPC ............. *G01N 11/00* (2013.01); *G01N 11/14* (2013.01); *G01N 2011/0006* (2013.01)

(58) Field of Classification Search
CPC .............. G01N 11/00; G01N 11/14; G01N 2011/0006; G01N 2011/0026; G01N 2011/006

USPC ... 73/1.01, 1.02, 54.01, 54.02, 54.23, 54.28, 73/54.37, 54.38, 54.39, 1.03
See application file for complete search history.

(56) References Cited

U.S. PATENT DOCUMENTS

| | | |
|---|---|---|
| 5,012,667 A | 5/1991 | Kruse |
| 5,509,297 A | 4/1996 | Miiller et al. |
| (Continued) | | |

FOREIGN PATENT DOCUMENTS

| | | | |
|---|---|---|---|
| WO | 9004161 A1 | 4/1990 | |

OTHER PUBLICATIONS

High-Shear Viscometry with a Rotational Parallel—Disk Device, R. W. Connelly and J. Greener, View Affiliations, Journal of Rheology 29, 209 (1985).*

(Continued)

*Primary Examiner* — Laura Martin
*Assistant Examiner* — Suman K Nath
(74) *Attorney, Agent, or Firm* — McDermott Will & Emery LLP

(57) ABSTRACT

Shear thinning fluids may be useful as calibration fluids for calibrating rheometers with bob/rotor eccentricity and at lower shear rates, which may be particularly useful for calibrating rheometers at well sites that are used for measuring the rheological properties of complex fluids (e.g., wellbore fluids like drilling fluids, cementing fluids, fracturing fluids, completion fluids, and workover fluids). Additionally, high shear rate calibrations may also be performed with shear thinning calibration fluids. Newtonian fluids may be used for high shear rate calibrations in alternate of or in addition to the shear thinning calibration fluid.

10 Claims, 3 Drawing Sheets

(56) References Cited

U.S. PATENT DOCUMENTS

| | | | | |
|---|---|---|---|---|
| 2004/0149019 A1* | 8/2004 | Johnson | ............... | G01N 11/14 73/54.28 |
| 2012/0247190 A1* | 10/2012 | Brown | ................. | G01N 11/08 73/54.09 |
| 2012/0260723 A1* | 10/2012 | Brookfield | ............ | G01N 11/14 73/54.01 |
| 2014/0262516 A1 | 9/2014 | Larson | | |
| 2014/0311225 A1 | 10/2014 | Morgan et al. | | |

OTHER PUBLICATIONS

High shear rate viscometry, Christopher J. Pipe, Trushant S. Majmudar, Gareth H McKinley, Rheol Acta (2008) 47:621-642.*

Official Action for Australian Patent Application No. 2014384848 dated Jan. 12, 2016.

Pan, L. et al, 'A high-shear, low Reynolds number microfluidic rheometer', Microfluidics and Nanofluidics. 2013, vol. 14, issue 5, pp. 885-894.

Siginer et al., Flow of Drilling Fluids Between Eccentric Rotating Cylinders, Annual Transactions of the Nordic Rheology Society, vol. 4, 59 (1996).

Chhabra R.P., Bubbles, Drops and Particles in Non-Newtonian Fluids, Taylor & Francis, New York (2007), pp. 129 and 130.

Chhabra, R. P., Bubbles, Drops, and Particles in Non-Newtonian Fluids, Second Edition, Taylor & Francis Group LLC, 2007, p. 16.

International Search Report and Written Opinion for PCT/US2014/063388 dated Jul. 17, 2015.

* cited by examiner

SHEAR THINNING CALIBRATION FLUIDS FOR RHEOMETERS AND RELATED METHODS

BACKGROUND

The present disclosure relates to calibration fluids for rheometers and the related methods.

A drilling fluid or mud is a specially designed fluid that is circulated through a wellbore as the wellbore is being drilled to facilitate the drilling operation. The various functions of a drilling fluid include removing drill cuttings from the wellbore, cooling and lubricating the drill bit, aiding in support of the drill pipe and drill bit, and providing a hydrostatic head to maintain the integrity of the wellbore walls and prevent well blowouts. Specific drilling fluid systems are selected to optimize a drilling operation in accordance with the characteristics of a particular geological formation. For the drilling fluid to perform its functions, its optimum chemical and rheological properties must be controlled.

One property of the drilling fluid that is of interest is its rheology, and specific rheological properties may be desired for drilling and circulating the fluid through the wellbore. Generally, the drilling fluid should be sufficiently viscous to suspend drilled cuttings and other particulates and to carry the cuttings to the well surface. However, the drilling fluid should not be so viscous as to interfere with the drilling operation. To achieve such properties, drilling fluids are often complex fluids with several components like the base fluid, a weighting agent, a suspending agent, a viscosifier, and a fluid loss control agent.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
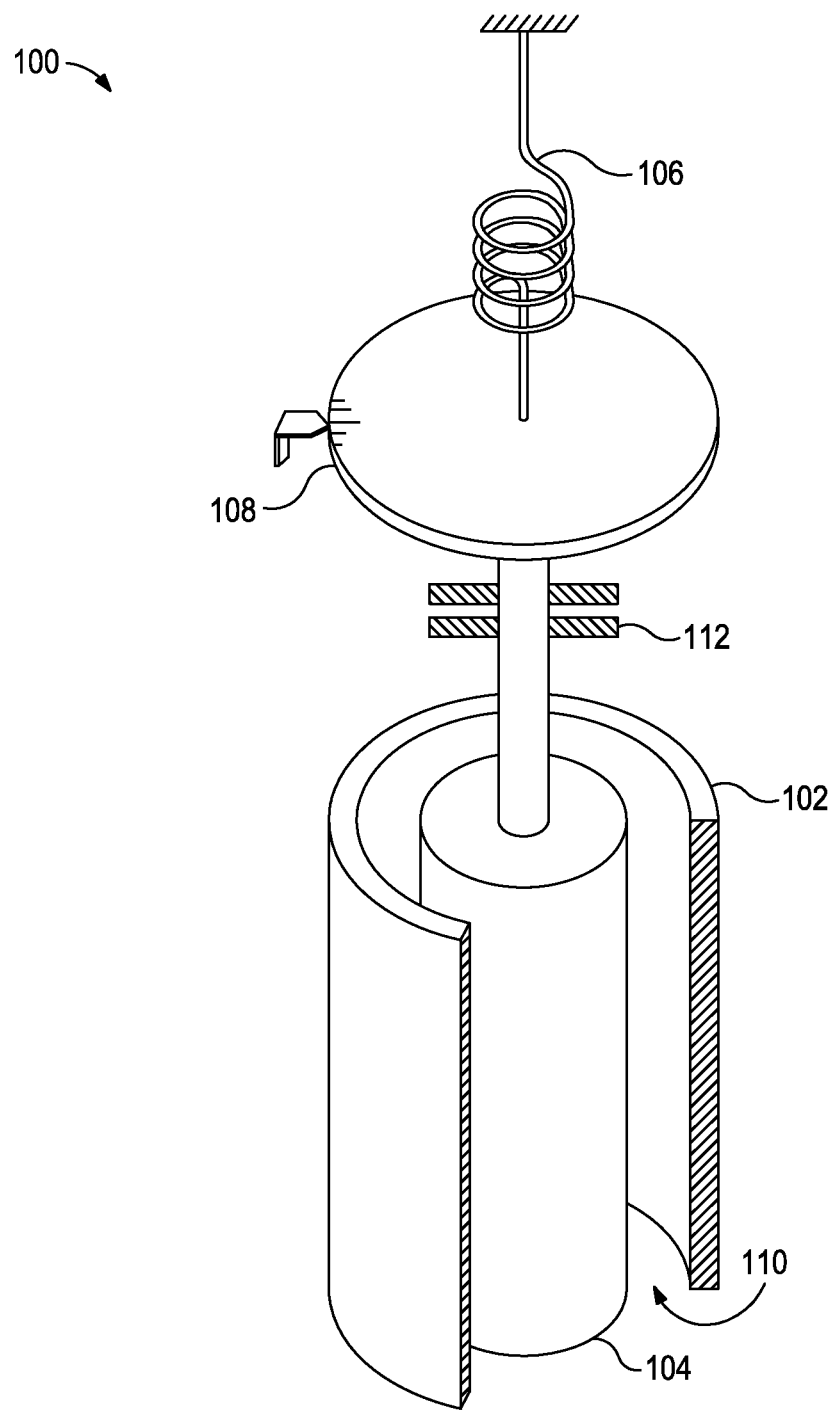
FIG. 1 illustrates the rotor and bob portion of an exemplary rheometer.

The present disclosure relates to calibration fluids for rheometers and the related methods. More specifically, the present disclosure relates to shear thinning calibration fluids for use in calibrating rheometers with bob/rotor eccentricity and at lower shear rates, which may be particularly useful for calibrating rheometers at well sites that are used for measuring the rheological properties of complex fluids (e.g., wellbore fluids like drilling fluids, cementing fluids, fracturing fluids, completion fluids, and workover fluids).

As used herein, the term "rheometer" is used generally to describe rheometers and viscometers and encompasses instrumentation like pipe or capillary rheometers, rotational cylinder rheometers, parallel plate rheometers, cone and plate rheometers, linear shear rheometers, oil-field viscometers that measure shear stress at different shear rates in a rotational cylinder setup, controlled stress rheometers, and controlled strain rheometers.

Various calibration methods and steps are discussed herein. In some contexts, calibrating may comprise an operation that (1) measures a standard sample under specified experimental conditions, (2) compares (a) the measurements of the standard sample to (b) a known value for the standard sample under the specified conditions, and (3) applies a correction factor, if needed, to correct the raw data obtained in measuring a sample. In some instances, such as when there is little or no discrepancy between the measured value and the known value, calibrating may involve only (1) measuring the standard sample and (2) comparing the measurement of the standard sample and the known value, because the measurement is within specification (i.e., within a predetermined set of limits based on the known value for the standard sample).

In some embodiments, the correction factor may be a mathematical correlation or functionality between (a) the standard sample under specified experimental conditions and (b) the known value for the standard sample. In some embodiments, the correction factor may be a physical adjustment to a component of the rheometer (e.g., tightening or loosening a tension spring or altering the relative positions of the bob and rotor).

As used herein, the term "Newtonian fluid" refers to a fluid having a linear or near-linear relationship between shear stress ($\tau$) and strain rate (or shear rate ($\dot{\gamma}$)). The slope of the relationship is often referred to as Newtonian viscosity ($\mu$) and is provided in Equation 1.

$$\mu = \frac{\tau}{\dot{\gamma}} \quad \text{Equation 1}$$

Examples of Newtonian fluids may include, but are not limited to, water, brines, mineral oil, silicone oils, and the like.

Various shear-thinning fluids, and associated methods and method steps involving shear-thinning fluids, are discussed herein. The term "shear-thinning fluid" may refer to a non-Newtonian fluid where the viscosity (a measure of a fluid's resistance to flow) decreases with increasing shear stress or shear rate. Shear thinning fluids may also be described as pseudoplastic fluids, Bingham plastics, or Herschel-Bulkley fluids. Examples of shear-thinning fluids may include, but are not limited to, ketchup, paint, nanoparticle suspensions, polymer solutions, molten polymers, some wellbore fluids (e.g., drilling fluids, cementing fluids, fracturing fluids, completion fluids, and workover fluids), and the like.

FIG. 1 illustrates the rotor 102 (sometimes referred to as a cup) and bob 104 portion of an exemplary rheometer 100. The bob 104 is attached to a torque measurement device (illustrated as a dial 108 but may alternatively be a position transducer or encoder). Together, these are typically supported by bearings 112 (e.g., ball bearings, flexure bearings, magnetic bearings, air bearings, and the like). The torsion spring 106 resists rotational torque of the sheared sample disposed in the annulus 110 between the rotor 102 and the bob 104. As the rotor 102 spins, torque is applied to the bob 104, which rotates the bob 104 and the dial 108 relative to the spring 106. The degree of rotation, which is proportional to the shear stress, may be read at the dial 108 and used to plot shear stress as a function of shear rate. Such a plot may then be used to derive a variety of rheological properties (e.g., viscosity, shear thinning index, viscosity index, yield stress, and gel strength).

By way of nonlimiting examples, Table 1 provides various dimensions for rotor and bob combinations.

TABLE 1

| | Rotor Radius (cm) | Bob Radius (cm) | Bob Height (cm) | Shear Gap in Annulus (cm) |
|---|---|---|---|---|
| 1 | 1.8415 | 1.7245 | 3.800 | 0.1170 |
| 2 | 1.7588 | 1.7245 | 3.800 | 0.0343 |
| 3 | 2.5866 | 1.7245 | 3.800 | 0.8621 |
| 4 | 1.8415 | 1.2276 | 3.800 | 0.6139 |
| 5 | 1.8415 | 0.8622 | 3.800 | 0.9793 |
| 6 | 1.8415 | 0.8622 | 1.900 | 0.9793 |

While FIG. 1 illustrates a rheometer 100 where the rotor 102 rotates, one skilled in the art would recognize that other rotational cylinder rheometers that operate in a different manner (e.g., a rotating bob). The calibration fluids and related methods described herein may be applied to these other rotational cylinder rheometers and the other types of rheometers described herein. Rheometers are calibrated by manufacturers by a variety of methods including the use of dead weights to calibrate the tension spring of rotational cylinder rheometers.

Generally, Newtonian calibration fluids, typically having a viscosity of about 20 cp to about 500 cp, are used at higher shear rates (e.g., greater than about 100 s$^{-1}$ and up to about 2,000 s$^{-1}$, but often greater than about 500 s$^{-1}$) to calibrate the torque measurement device of a rheometer, especially oil-field viscometers. However, because of the complexity of a wellbore fluid composition, the characterization of wellbore fluid rheology is often done at various rotational speeds including 3 rpm, 6 rpm, 100 rpm, 200 rpm, 300 rpm, and 600 rpm, which correspond to shear rates of about 1 s$^{-1}$ to about 2000 s$^{-1}$ depending on the rheometer configuration. While Newtonian fluids have a linear relationship between shear rate and shear stress, they are not suitable for calibrating rheometers at lower shear rates (i.e., lower rotational speeds) because at such shear rates the Newtonian fluid yields torque within the rheometer that is comparable to the minimum resolution of the torque measurement device. By contrast, a shear thinning fluid has a greater viscosity at lower shear rates. Therefore, embodiments described herein may involve calibrating the rheometer at lower shear rates (e.g., less than about 100 s$^{-1}$ and as low as about 1 s$^{-1}$, or less than about 500 s$^{-1}$) with a shear thinning calibration fluid described herein. In alternate embodiments, the shear thinning calibration fluid may be used for calibrating at both high and low shear rates (e.g., at two or more points between about 1 to about 2000 s$^{-1}$).

When calibrating the rheometer with a shear thinning calibration fluid, under specified experimental conditions (e.g., temperature, pressure, and geometry) the shear thinning calibration fluid may have known shear stress profiles over a range of shear stresses or a known shear stress for one or more shear rates. Therefore, shear stress measurements from running the shear thinning calibration fluid at the specified experimental conditions may be correlated to the expected or standard shear stress values or profiles, which can be used in determining and applying the correction factor of the calibration operation. In some instances, if the measurements as compared to the expected shear stress values or profiles are too far out of specification, the rheometer may be repaired (e.g., on-site or in an off-site facility). In some instances, if the measurements as compared to the expected shear stress values or profiles are within specification, the calibration operation may involve just measuring the shear stress and comparing the measured shear stress to known values.

For shear thinning fluids, the rheological measurements on rotational cylinder rheometers and the values for the rheological properties derived therefrom are effected not only by the relative rotational speed of the rotor and the bob (which relates to shear rate) but also the eccentricity of the rotor and bob.

Figure 2:
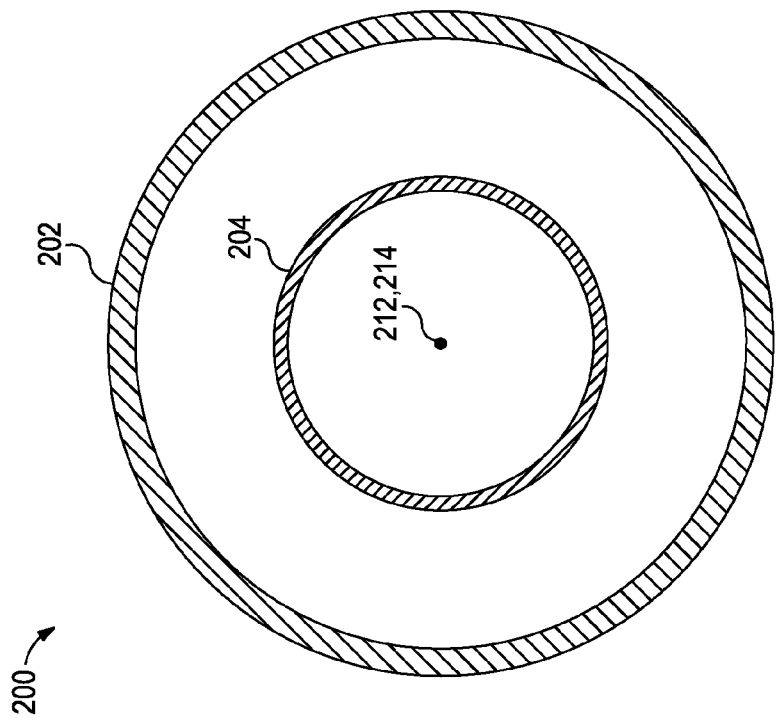
FIG. 2 illustrates a cross-section of an exemplary rheometer with an aligned or concentric rotor and bob.

FIG. 2 illustrates a cross-section of an exemplary rheometer 200 with an aligned or concentric rotor 202 and bob 204. That is, the central point 212 of the rotor 202 and the central point 214 of the bob 204 are the same. This aligned configuration is generally the preferred configuration and the configuration used when developing and establishing calibration fluids. Because the shear stress (i.e., torque in the rheometer) for Newtonian fluids is linearly proportional to shear rate, a positional offset or eccentricity of the rotor 202 and the bob 204 would negligibly impact the measurements, and therefore, go undetected. In contrast, because the shear stress for a shear thinning fluid has a non-linear relation with shear rate and because the shear thinning fluid may have a yield stress, eccentricity of the rotor 202 and the bob 204 may lead to significant deviation in the rheometer measurements. Because wellbore fluids (e.g., drilling fluids, cementing fluids, fracturing fluids, completion fluids, and workover fluids) often have shear thinning characteristics, un-detected eccentricity, which may arise from only calibrating with Newtonian fluids, may lead to incorrect rheometer measurements and, consequently, incorrect drilling parameters. Using the incorrect drilling parameters relative to a specified wellbore fluid may result in inefficient wellbore operations, subterranean formation damage (e.g., unintended fracturing at the wellbore), or well control issues during drilling or wellbore fluid placement (i.e., lost circulation or kicks). Therefore, embodiments described herein may involve calibrating the eccentricity of the rheometer with a shear thinning calibration fluid described herein.

Figure 3:
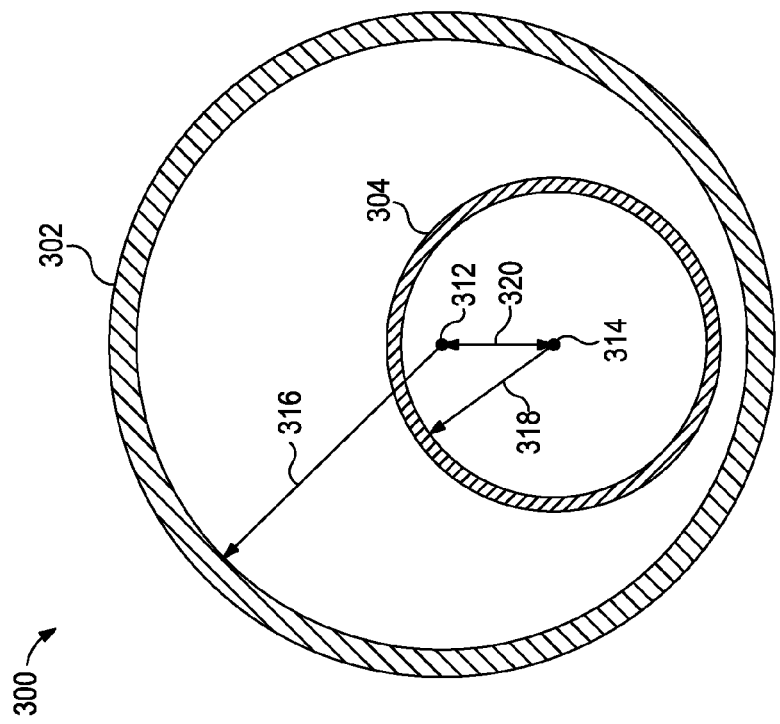
FIG. 3 illustrates a cross-section of an exemplary rheometer having a bob that is eccentric relative to a rotor.

FIG. 3 illustrates a cross-section of an exemplary rheometer 300 having a bob 304 that is eccentric relative to a rotor 302. As used herein, the term "eccentric" refers not centrally placed. That is, the central point 312 of the rotor 302 and the central point 314 of the bob 304 are in different locations. The annulus eccentricity ($\epsilon$) can be defined by Equation 2, which is the distance between the two central points 312,314 (referred to as b in Equation 2 and illustrated as 320 in FIG. 3) divided by the difference between the radii 316,318 of the rotor 302 and the bob 304 (referred to as $r_2$ and $r_1$, respectively, in Equation 2).

$$\varepsilon = \frac{b}{r_2 - r_1} \qquad \text{Equation 2}$$

When calibrating for eccentricity, two calibration procedures are performed, preferably, at the same shear rate(s)—high shear rate calibration with a Newtonian fluid and eccentricity calibration with a shear thinning fluid. The high shear rate calibration accounts for calibration corrections (mathematical or physical) that also effect the shear stress behavior of the shear thinning fluid. For example, the high shear rate calibration may necessitate adjustment of the tension spring, so that the shear stress measurements are accurate. Alternatively, the high shear rate calibration may provide a mathematical correction that is applied to measured shear stress, which is applied to the shear stress values for the shear thinning fluid to provide accurate measurements for eccentricity calibration.

For the eccentricity calibration with the shear thinning fluid, the shear thinning calibration fluid may have known shear stress value(s) or shear stress profile(s) at the specified shear rate values (i.e., preferably shear rates that correspond to the those of the high shear rate calibration with the Newtonian fluid) for various eccentricity values under specified experimental conditions (e.g., rotational speed, temperature, and the like). Therefore, measurements from running the shear thinning calibration fluid at the specified experimental conditions may be correlated to an eccentricity value, which can be used in determining and applying the correction factor of the calibration operation. In some instances, if the eccentricity value is too far out of specification, the rheometer may be repaired (e.g., on-site or in an off-site facility). In some instances, if the eccentricity value (or the shear stress measurements of the shear thinning fluid at the specified shear rate(s)) is within specification, the eccentricity calibration operation may involve just measuring the shear stress of the shear thinning fluid and comparing the measured shear stress to known values.

In some embodiments, the calibration methods described herein (e.g., low shear rate calibration with a shear thinning calibration fluid, eccentricity calibration with a shear thinning calibration fluid, high shear rate with a Newtonian calibration fluid or a shear thinning fluid, or combinations thereof) may be performed at two or more temperatures. Performing calibrations at two or more temperatures may be useful when the rheological properties of subsequent samples are to be measured at various temperatures.

In some embodiments, calibration may involve performing a high shear rate calibration (shear rate greater than about 100 s$^{-1}$) with a Newtonian fluid and also performing a low shear rate calibration (shear rate less than about 100 s$^{-1}$) with a shear-thinning fluid at a second shear rate that is less than the first shear rate. After calibration fluids are run, at least one known rheological property of each of the tested samples (the Newtonian fluid and the shear-thinning) is compared with reading from the rheometer being calibrated. In various embodiments, the second shear rate may be about 10%, about 15%, about 20%, about 25%, about 30%, about 35%, about 40%, about 45%, about 50%, about 55%, about 60%, about 65%, about 70%, or about 75% lower than the first shear rate. That is, if the first shear rate is 100 s$^{-1}$ and the second shear rate is about 30% lower than the first shear rate then the second shear rate will be about 70 s$^{-1}$. About as used herein generally refers to a number within 5% of the stated value such that about 70 s$^{-1}$ refers to a value of 66.5 s$^{-1}$ to 715 s$^{-1}$.

Generally, calibration of the rheometer by the methods described herein may be done on-demand and/or at any desired interval time (e.g., weekly, monthly, etc.). For example, rheometers located in laboratories are generally stable for longer periods of time than rheometers in the field (e.g., at a well site) because the storage, cleaning, and operating conditions are more controlled either as a result of the environment or the actions of the operators.

After calibration of the rheometer by the methods described herein, the rheological properties for samples may be measured. Examples of rheological properties may include, but are not limited to, shear stress, viscosity, shear thinning index, viscosity index, plastic viscosity (PV), yield point (YP), low shear yield point (LSYP), yield stress, gel strength, and the like, and any combination thereof.

In some embodiments, the samples tested may be wellbore fluids (e.g., drilling fluids, cementing fluids, fracturing fluids, completion fluids, and workover fluids) and the rheometer may be at a well site. In some embodiments, the samples tested may be wellbore fluids, and the rheometer may be in a laboratory.

Shear thinning calibration fluids should preferably be stable for long periods of time (e.g., at least 6 months, or preferably at least 1 year), have few components so that it is easy to reproducibly formulate, and have sufficient viscosity at low shear rates for calibration purpose.

In some embodiments, a shear thinning calibration fluid may have an apparent viscosity at a shear rate of 5 s$^{-1}$ ranging from a lower limit of about 50 cP, 100 cP, 500 cP, or 1,000 cP to an upper limit of about 30,000 cP, 10,000 cP, or 5,000 cP, and wherein the apparent viscosity may range from any lower limit to any upper limit and encompass any subset therebetween.

Examples of shear thinning calibration fluids may include, but are not limited to, colloidal suspensions, polymer solutions, stabilized emulsions, microemulsions, worm-like micelle solutions, and any combination thereof (each described in more detail herein).

The continuous phase of a shear thinning calibration fluid may be aqueous or non-aqueous. The non-aqueous fluid examples are alkanes, olefins, aromatic organic compounds, cyclic alkanes, paraffins, diesel fluids, mineral oils, silicone oils, desulfurized hydrogenated kerosenes, esters, and any combination thereof. Examples of aqueous liquids may include fresh water, saltwater (e.g., water containing one or more salts dissolved therein), brine (e.g., saturated salt water), seawater, and the like, and any combination thereof. Examples of aqueous-miscible fluids may include, but not be limited to, alcohols (e.g., methanol, ethanol, n-propanol, isopropanol, n-butanol, sec-butanol, isobutanol, and t-butanol), glycerins, glycols (e.g., polyglycols, propylene glycol, and ethylene glycol), polyglycol amines, polyols, any derivative thereof, any in combination with salts (e.g., sodium chloride, calcium chloride, calcium bromide, zinc bromide, potassium carbonate, sodium formate, potassium formate, cesium formate, sodium acetate, potassium acetate, calcium acetate, ammonium acetate, ammonium chloride, ammonium bromide, sodium nitrate, potassium nitrate, ammonium nitrate, ammonium sulfate, calcium nitrate, sodium carbonate, potassium carbonate, and any combination thereof), and the like, and any combination thereof. Combinations of aqueous fluids and aqueous miscible fluids may also be suitable as the continuous phase of the shear thinning calibration fluid. The term "derivative" is defined herein to include any compound that is made from one of the listed compounds, for example, by replacing one atom in the listed compound with another atom or group of atoms, rearranging two or more atoms in the listed compound, ionizing the listed compounds, or creating a salt of the listed compound.

Examples of particulates suitable for producing colloidal suspensions may include, but are not limited to, barite, poly(methyl methacrylate) (PMMA) particles, hematite, ilmenite, galena, manganese oxide, iron oxide, magnesium tetroxide, magnetite, siderite, celesite, manganese carbonate, galena, magnetite, dolomite, calcium carbonate, marble, glass bubbles, olive stone, polyethylene, polypropylene, graphitic materials, silica, limestone, dolomite, a salt (e.g., salt crystals), shale, bentonite, kaolinite, sepiolite, illite, hectorite, organoclays, and the like, and any combination thereof. Such particulates may have a number average diameter ranging from a lower limit of about 1 nm, 5 nm, 10 nm, 50 nm, or 100 nm to an upper limit of about 1000 microns, 500 microns, 10 microns, 1 micron, 500 nm, or 100 nm, and wherein the number average diameter may range from any lower limit to any upper limit and encompass any subset therebetween.

Examples of polymers suitable for producing polymer solutions may include, but are not limited to, polysaccharides, guar gums (e.g., hydroxyethyl guar, hydroxypropyl guar, carboxymethyl guar, carboxymethylhydroxyethyl guar, and carboxymethylhydroxypropyl guar ("CMHPG")), cellulose derivatives (e.g., hydroxyethyl cellulose, carboxyethylcellulose, carboxymethylcellulose, and carboxymethylhydroxyethylcellulose), xanthan, scleroglucan, succinoglycan, diutan, alginate, chitosan, curdlan, dextran, emulsan, gellan, glucuronan, N-acetyl-glucosamine, N-acetyl-heparosan, hyaluronic acid, kefiran, lentinan, levan, mauran, pullulan, scleroglucan, schizophyllan, stewartan, succinoglycan, wean, derivatized starch, tamarind, tragacanth, gum ghatti, gum arabic, locust bean gum, poly(vinyl acetate), poly(ethylene glycol), poly(vinyl pyrrolidone), 2,2'-azobis (2,4-dimethyl valeronitrile), 2,2'-azobis(2,4-dimethyl-4-methoxy valeronitrile), polymers and copolymers of acrylamide ethyltrimethyl ammonium chloride, acrylamide, acrylamido- and methacrylamido-alkyl trialkyl ammonium salts, acrylamidomethylpropane sulfonic acid, acrylamidopropyl trimethyl ammonium chloride, acrylic acid, dimethylaminoethyl methacrylamide, dimethylaminoethyl methacrylate, dimethylaminopropyl methacrylamide, dimethylaminopropylmethacrylamide, dimethyldiallylammonium chloride, dimethylethyl acrylate, fumaramide, methacrylamide, methacrylamidopropyl trimethyl ammonium chloride, methacrylamidopropyldimethyl-n-dodecylammonium chloride, methacrylamidopropyldimethyl-n-octylammonium chloride, methacrylamidopropyltrimethylammonium chloride, methacryloylalkyl trialkyl ammonium salts, methacryloylethyl trimethyl ammonium chloride, methacrylylamidopropyldimethylcetylammonium chloride, N-(3-sulfopropyl)-N-methacrylamidopropyl-N,N-dimethyl ammonium betaine, N,N-dimethylacrylamide, N-methylacrylamide, nonylphenoxypoly(ethyleneoxy)ethylmethacry late, partially hydrolyzed polyacrylamide, poly 2-amino-2-methyl propane sulfonic acid, polyvinyl alcohol, sodium 2-acrylamido-2-methylpropane sulfonate, quaternized dimethylaminoethylacrylate, quaternized dimethylaminoethylmethacrylate, any derivative thereof, and the like, and any combination thereof.

As used herein, the term "emulsion" refers to a thermodynamically unstable liquid mixture of oil, water, and an amphiphile (e.g., surfactants, polymers, or any combination thereof). The formation of emulsions generally required an input of work (e.g., high shear mixing). As used herein, the term "microemulsion" refers to a thermodynamically stable, isotropic liquid mixture of oil, water, and an amphiphile (e.g., surfactants, polymers, or any combination thereof). In contrast to emulsions, microemulsions may be formed upon simple mixing of the components and do not necessarily require high shear conditions. Further, microemulsions generally have droplet sizes of about 5 nm to about 100 nm, while emulsions generally have droplet sizes greater than about 100 nm. The larger droplet size of emulsions often provides for a milky or turbid appearance as compared to a generally translucent appearance of microemulsions.

The emulsions may be water-in-oil emulsions, or oil-in-water emulsions. The oil phase may be any of the compositions provided in the non-aqueous fluid examples described herein. The water phase may be any of the compositions provided in the aqueous fluid and aqueous-miscible fluid examples described herein. Water-in-oil emulsions, also known as invert emulsions, may have an oil-to-water ratio from a lower limit of greater than about 50:50, 55:45, 60:40, 65:35, 70:30, 75:25, or 80:20 to an upper limit of less than about 100:0, 95:5, 90:10, 85:15, 80:20, 75:25, 70:30, or 65:35 by volume in the base treatment fluid, where the amount may range from any lower limit to any upper limit and encompass any subset therebetween.

As used herein, the term "stabilized emulsion" refers to an emulsion that has been thermodynamically stabilized with the addition or inclusion of an emulsifier, a polymer, a crosslinker, particulates (e.g., stabilized via the Pickering mechanism), and any combination thereof.

Examples of emulsifiers suitable for stabilizing emulsions may include, but are not limited to, fatty acid derivatives (e.g., fatty acid amides consisting of N-alkylated poly(ether) chains), citric acid-based polyamide-type emulsifiers, imidazolines-based polyamide surfactants, sodium stearoyl lactylate, lecithin, mustard, soy lecithin, diacetyl tartaric (acid) ester of monoglyceride, emulsifying wax, cetearyl alcohol, polysorbate, ceteareth, and the like, and any combination thereof.

Examples of polymers suitable for stabilizing emulsions may include those provided herein relative to polymer solutions.

Examples of surfactants and compounds suitable for forming worm-like micelle solutions may include, but are not limited to, methyl ester sulfonates; hydrolyzed keratin; sulfosuccinates; taurates; amine oxides; ethoxylated amides; alkoxylated fatty acids; alkoxylated alcohols (e.g., lauryl alcohol ethoxylate, ethoxylated nonyl phenol); ethoxylated fatty amines; ethoxylated alkyl amines (e.g., cocoalkylamine ethoxylate); betaines; modified betaines; alkylamidobetaines (e.g., cocoamidopropyl betaine); quaternary ammonium compounds (e.g., trimethyltallowammonium chloride and trimethylcocoammonium chloride); mixtures of an ammonium salt of an alkyl ether sulfate, a cocoamidopropyl betaine surfactant, a cocoamidopropyl dimethylamine oxide surfactant, sodium chloride, and water; mixtures of an ammonium salt of an alkyl ether sulfate surfactant, a cocoamidopropyl hydroxysultaine surfactant, a cocoamidopropyl dimethylamine oxide surfactant, sodium chloride, and water; mixtures of an ethoxylated alcohol ether sulfate surfactant, an alkyl or alkene amidopropyl betaine surfactant, and an alkyl or alkene dimethylamine oxide surfactant; aqueous solutions of an alpha-olefinic sulfonate surfactant and a betaine surfactant; oleate (NaO)/octyl trimethylammonium chloride (C8TAC) systems; stearyl trimethylammonium chloride (C18TAC)/caprylic acid sodium salt (NaCap) systems; and cetyl trimethylammonium tosylate (CTAT)/ sodium dodecylbenzenesulfonate (SDBS) systems; and any combination thereof. One of skill in the art would recognize concentration of the surfactant(s) suitable for forming worm-like micelles, which, depending on the surfactant system, may be about 0.1% to about 20% by weight of the fluid.

In some embodiments, other additives may optionally be included in a shear thinning calibration fluid. Examples of such additives may include, but are not limited to, salts, weighting agents, dispersion aids, corrosion inhibitors, emulsion thinners, emulsion thickeners, viscosifying agents, surfactants, pH control additives, anti-foaming agents, breakers, biocides, crosslinkers, stabilizers and any combination thereof.

Figure 4:
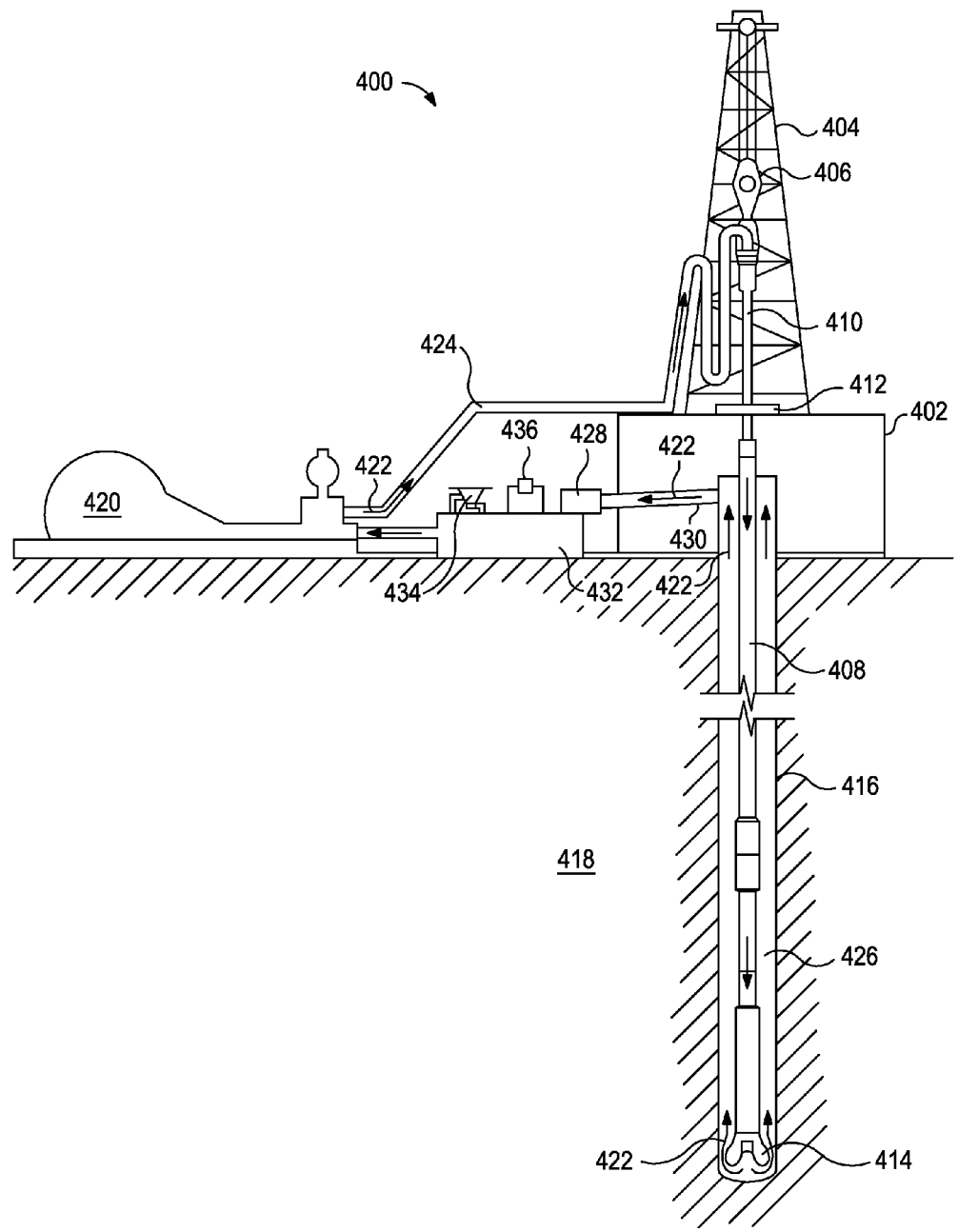
FIG. 4 illustrates a wellbore drilling assembly 400 according to one or more embodiments.

As described herein, the rheometer may be located at a well site. FIG. 4 illustrates a wellbore drilling assembly 400 according to one or more embodiments. It should be noted that while FIG. 4 generally depicts a land-based drilling assembly, those skilled in the art will readily recognize that the principles described herein are equally applicable to subsea drilling operations that employ floating or sea-based platforms and rigs, without departing from the scope of the disclosure.

As illustrated, the drilling assembly 400 may include a drilling platform 402 that supports a derrick 404 having a traveling block 406 for raising and lowering a drill string 408. The drill string 408 may include, but is not limited to, drill pipe and coiled tubing, as generally known to those skilled in the art. A kelly 410 supports the drill string 408 as it is lowered through a rotary table 412. A drill bit 414 is attached to the distal end of the drill string 408 and is driven either by a downhole motor and/or via rotation of the drill string 408 from the well surface. As the bit 414 rotates, it creates a borehole 416 that penetrates various subterranean formations 418.

A pump 420 (e.g., a mud pump) circulates drilling fluid 422 through a feed pipe 424 and to the kelly 410, which conveys the drilling fluid 422 downhole through the interior of the drill string 408 and through one or more orifices in the drill bit 414. The drilling fluid 422 is then circulated back to the surface via an annulus 426 defined between the drill string 408 and the walls of the borehole 416. At the surface, the recirculated or spent drilling fluid 422 exits the annulus 426 and may be conveyed to one or more fluid processing unit(s) 428 via an interconnecting flow line 430. After passing through the fluid processing unit(s) 428, a "cleaned" drilling fluid 422 is deposited into a nearby retention pit 432 (i.e., a mud pit). While illustrated as being arranged at the outlet of the wellbore 416 via the annulus 426, those skilled in the art will readily appreciate that the fluid processing unit(s) 428 may be arranged at any other location in the drilling assembly 400 to facilitate its proper function, without departing from the scope of the disclosure.

A rheometer 436 may be included at the drilling assembly 400. The rheometer 436 may be in-line with one or more components of the drilling assembly 400. For example, as illustrated, the rheometer 436 may be in fluid communication with the retention pit 432 so as to measure and monitor the rheology of the drilling fluid therein. This may allow for further formulation of the drilling fluid (e.g., the addition of additional drilling fluid components) to achieve the desired rheological properties of the drilling fluid. Alternatively, not shown, a rheometer may be off-line such that an operator takes a drilling fluid sample from the drilling assembly and measures the rheological properties with the off-line rheometer. One skilled in the art would recognized the other in-line and off-line configurations for including one or more rheometers in the drilling assembly 400.

A drilling fluid 422 may be formulated or mixed using a mixing hopper 434 communicably coupled to or, otherwise, in fluid communication with the retention pit 432. The mixing hopper 434 may include, but is not limited to, mixers and related mixing equipment known to those skilled in the art. In other embodiments, however, the drilling fluid 422 may be formulated or mixed at any other location in the drilling assembly 400. In at least one embodiment, for example, there could be more than one retention pit 432, such as multiple retention pits 432 in series. Moreover, the retention pit 432 may be representative of one or more fluid storage facilities and/or units where drilling fluid components may be stored, reconditioned, and/or regulated until added to the drilling fluid 422.

While not specifically illustrated herein, the drilling assembly 400 may further include transport or delivery equipment used to convey the drilling fluid or components thereof such as, for example, any transport vessels, conduits, pipelines, trucks, tubulars, and/or pipes used to fluidically move the drilling fluid or components from one location to another, any pumps, compressors, or motors used to drive the drilling fluid or components into motion, any valves or related joints used to regulate the pressure or flow rate of the drilling fluid or components, and any sensors (i.e., pressure and temperature), gauges, and/or combinations thereof, and the like.

Embodiments disclosed herein include:

Embodiment A. a method that includes: calibrating a rheometer including performing a high shear rate calibration on the rheometer with a Newtonian fluid at a first shear rate greater than about 100 $s^{-1}$ and performing a low shear rate calibration on the rheometer with a shear-thinning fluid at a second shear rate that is less than the first shear rate, thereby yielding a calibrated rheometer; and measuring at least one rheological property of a sample with the calibrated rheometer;

Embodiment B. a method that includes: calibrating a rheometer including performing a high shear rate calibration on the rheometer with a shear thinning fluid at a first shear rate greater than about 100 $s^{-1}$ and performing a low shear rate calibration on the rheometer with the shear-thinning fluid at a second shear rate that is less than the first shear rate, thereby yielding a calibrated rheometer; and measuring at least one rheological property of a sample with the calibrated rheometer; and Embodiment C. a method that includes: calibrating a rheometer including performing a high shear rate calibration on the rheometer with a Newtonian fluid at one or more shear rates and performing an eccentricity calibration on the rheometer with a shear-thinning fluid at the one or more shear rates, thereby yielding a calibrated rheometer; and measuring at least one rheological property of a sample with the calibrated rheometer.

Each of Embodiments A, B, and C may have one or more of the following additional elements in any combination: Element 1: wherein the first shear rate is greater than about 500 $s^{-1}$; Element 2: wherein calibrating the rheometer is performed at two or more temperatures; Element 3: wherein the shear thinning fluid has an apparent viscosity of about 50 cP to about 30,000 cP at a shear rate of 5 $s^{-1}$; Element 4: wherein the sample is a wellbore fluid and the method is performed at a well site; Element 5: Element 4 and wherein the wellbore fluid is a drilling fluid and the method further comprises: drilling at least a portion of a wellbore penetrating a subterranean formation with the drilling fluid; Element 6: wherein the sample is a wellbore fluid and the method is performed at a laboratory; Element 7: wherein the at least one rheological property includes one selected from the group consisting of: a shear stress, a viscosity, a shear thinning index, a viscosity index, a plastic viscosity, a yield point, a low shear yield point, a yield stress, and a gel strength; Element 8: wherein the shear-thinning fluid comprises at least one selected from the group consisting of: a colloidal suspension, a polymer solution, a stabilized emulsion, a microemulsion, a worm-like micelle solution, and any combination thereof; and Element 9: wherein calibrating the rheometer further involves performing an eccentricity calibration with the shear-thinning fluid at the first shear rate.

By way of non-limiting example, exemplary combinations applicable to Embodiments A, B, and C include: at least two of Elements 1-3 in combination; at least two of Elements 7-9 in combination; at least one of Elements 1-3 in combination with a least one of Elements 7-9; Element 6 or Element 4 optionally with Element 5 in combination with any of the foregoing; Element 4 optionally with Element 5 in combination with a least one of Elements 1-3; Element 4 optionally with Element 5 in combination with a least one of Elements 7-9; Element 6 in combination with a least one of Elements 1-3; and Element 6 in combination with a least one of Elements 7-9.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill the art and having benefit of this disclosure.

While compositions and methods are described herein in terms of "comprising" various components or steps, the compositions and methods can also "consist essentially of" or "consist of" the various components and steps.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles a" or "an," as used in the claims, are defined herein to mean one or more than one of the element that it introduces.

The invention claimed is:

1. A method comprising:
   calibrating a rheometer including performing a first shear rate calibration on the rheometer with a Newtonian fluid at a first shear rate greater than about 100 $s^{-1}$ and performing a second shear rate calibration on the rheometer with a shear-thinning fluid at a second shear rate that is less than the first shear rate, thereby yielding a calibrated rheometer; and
   measuring at least one rheological property of a sample with the calibrated rheometer.

2. The method of claim 1, wherein the first shear rate is greater than about 500 $s^{-1}$.

3. The method of claim 1, wherein calibrating the rheometer is performed at two or more temperatures.

4. The method of claim 1, wherein the shear thinning fluid has an apparent viscosity of about 50 cP to about 30,000 cP at a shear rate of 5 $s^{-1}$.

5. The method of claim 1, wherein the sample is a wellbore fluid and the method is performed at a well site.

6. The method of claim 5, wherein the wellbore fluid is a drilling fluid and the method further comprises: drilling at least a portion of a wellbore penetrating a subterranean formation with the drilling fluid.

7. The method of claim 1, wherein the sample is a wellbore fluid and the method is performed at a laboratory.

8. The method of claim 1, wherein the at least one rheological property includes one selected from the group consisting of: a shear stress, a viscosity, a shear thinning index, a viscosity index, a plastic viscosity, a yield point, a low shear yield point, a yield stress, and a gel strength.

9. The method of claim 1, wherein the shear-thinning fluid comprises at least one selected from the group consisting of: a colloidal suspension, a polymer solution, a stabilized emulsion, a microemulsion, a worm-like micelle solution, and any combination thereof.

10. The method of claim 1, wherein calibrating the rheometer further involves performing an eccentricity calibration with the shear-thinning fluid at the first shear rate.

* * * * *